United States Patent [19]
Witiak et al.

[11] Patent Number: 5,185,366
[45] Date of Patent: Feb. 9, 1993

[54] METHOD FOR TREATMENT AND PREVENTION OF DISEASES CAUSED BY ENVELOPED VIRUSES, INCLUDING HERPES SIMPLEX VIRUS TYPES 1 AND 2 DISEASES, USING 3,4-DIHYDROXY-2H-BENZOPYRAN-2H-ONE

[75] Inventors: Donald T. Witiak, Mt. Vernon; John H. Hughes; Charis T. Mavromoustakis, both of Columbus, all of Ohio

[73] Assignee: Ohio State University Research Foundation, Columbus, Ohio

[21] Appl. No.: 561,015

[22] Filed: Jul. 31, 1990

[51] Int. Cl.$^5$ .............................. A61K 31/35
[52] U.S. Cl. ........................... 514/456; 514/457
[58] Field of Search ..................... 514/456, 457

[56] References Cited

U.S. PATENT DOCUMENTS

| | | | |
|---|---|---|---|
| 4,105,784 | 8/1978 | Okada | 424/283 |
| 4,352,792 | 10/1982 | Ishitsuka et al. | 424/180 |
| 4,845,121 | 7/1989 | Witiak et al. | 514/455 |

FOREIGN PATENT DOCUMENTS 0025599 12/1980 European Pat. Off. .

OTHER PUBLICATIONS

Ghosh, K. C., J. Indian Chem. Co., 24:323 (1947).
Witiak et al., J. Med. Chem., 25:90 (1982).
Mehl et al., Antimicrob. Agents Chemother., 18:269 (1980).
Steinhart et al., Virology, 70:241 (1976).
Grossberg et al., Progr. Immunobiol. Standard, 5:289 (1972).
Grossberg et al., Perspect., Virol., 9:279 (1975).
Majuk et al., J. Virol., 24:883 (1977).
Snipes et al., Antimicrob. Agents Chemother., 11:98 (1977).
Kamanna et al., Lipids, 24:25 (1989).
Witiak et al., J Med Chem 1988, 31, pp. 1437–1445.

Primary Examiner—Frederick E. Waddell
Assistant Examiner—Russell Travers
Attorney, Agent, or Firm—Emch, Schaffer, Schaub & Porceilo Co.

[57] ABSTRACT

The present invention relates to the pharmaceutical use of 3,4-dihydroxybenzopyranone compounds in the treatment of diseases caused by enveloped viruses, including herpes simplex virus (HSV) types 1 and 2.

8 Claims, No Drawings

METHOD FOR TREATMENT AND PREVENTION OF DISEASES CAUSED BY ENVELOPED VIRUSES, INCLUDING HERPES SIMPLEX VIRUS TYPES 1 AND 2 DISEASES, USING 3,4-DIHYDROXY-2H-BENZOPYRAN-2H-ONE

This invention was made with the U.S. Government support under the U.S. Public Health Service Grant No. HL12740 from the National Heart Lung and Blood Institute. The Government has certain rights in this invention.

BACKGROUND OF THE INVENTION

The present invention relates to the pharmaceutical use of 3,4-dihydroxybenzopyranone compounds possessing aci-reductone functionalities in the treatment or prevention of diseases caused by enveloped viruses, such as the herpes viruses, including herpes simplex virus (HSV) types 1 and 2, mumps, measles, influenza and the like.

One benzopyranone aci-reductone compound was reported to have been synthesized using a lengthy synthetic route by Ghosh, K. C., *J. Indian Chem. Co.*, 24:323, (1947), from a salicylate compound. Reaction with acetoxyacetyl chloride afforded an intermediate compound (93%) which upon reaction with Na in refluxing benzene afforded benzopyranone aci-reductone compound 5 (no yield reported). Attempted repetition of the process described in Ghosh to convert the intermediate compound to benzopyranone acid-reductone 5 were unsuccessful. The benzopyranone aci-reductone 5 compound can be prepared, as described by Schank et al., *Chem. Ber.*, 114:1958 (1981), from 4-hydroxycoumarin.

The chemistry and lipid biology of novel aci-reductones having both vinylogous acid and biologically relevant redox functionalities have been investigated. The vinylogous acid-possessing aci-reductone of formula 1 below may mimic carboxylic acid-containing drugs such as the phenoxyacetic acids of formula 2 owing to their similar pka values as disclosed by Witiak et al., *J. Med. Chem.*, 25:90 (1982). However, during docking to a targeted redox enzyme, 2-hydroxytetronic acid aci-reductone 1, but not phenoxyacetic acid 2, reduce oxidated forms of metals and/or activated oxygen species in the catalytic site. Also, the oxidation of the aci-reductone compound by two successive one electron transfers generates the less water soluble nonionic dione 3 which may have enhanced hydrophobic binding at the active site and/or undergo covalent reaction with neighboring sulfhydro or amino nucleophiles at the more electron deficient 2-one carbon atom.

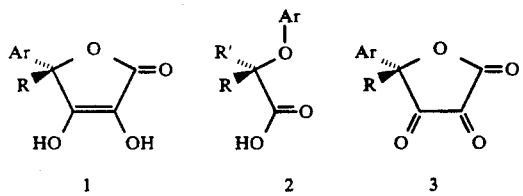

Previously, it was reported in Mehl et al., *Antimicrob. Agents Chemother.*, 18:269 (1980), that clofibric acid (2, R=R$_1$=Me, Ar=p—ClPh) inhibit replication of herpes simplex virus type 1 (HSV-1) in Buffalo green monkey kidney (BGM 70) cells. These studies confirm the antiherpetic activity of the antilipidemic drug clofibrate (clofibric acid ethyl ester) as disclosed in Steinhart et al., *Virology*, 70:241 (1976). Several other reports describe approaches to antiviral drug development based upon causing alterations of cellular lipid metabolism (Grossberg et al., *Progr. Immunobiol. Standard*, 5:289 (1972); Grossberg et al., *Perspect. Virol.*, 9:279 (1975)) to produce a defective lipid envelope, or a direct effect on the viral envelope, Majuk et al., *J. Virol.*, 24:883 (1977); Snipes et al., *Antimicrob. Agents Chemother.*, 11:98 (1977). Racemic 2-hydroxytetronic acid 1 (R=H, Ar=p—ClPh) exhibits a spectrum of antilipidemic properties different from those of clofibric acid (Kamanna et al., *Lipids*, 24:25 (1989)).

The use of the benzopyranone compound in an antiaggregatory composition is disclosed in the Witiak et al., U.S. Pat. No. 4,845,121, issued Jul. 4, 1989 to one of the co-inventors herein. These references, however, fail to suggest or mention the antiviral activity of benzopyranone aci-reductone compounds.

SUMMARY OF THE INVENTION

The present invention encompasses novel pharmaceutical compositions comprising 3,4-dihydroxy-2-benzopyran-2H-one together with a physiologically acceptable carrier or excipient, in an amount sufficient to have antiviral activities in an animal or patient. The compositions of the present invention are useful in the treatment or prevention of diseases caused by enveloped viruses, including for example, herpes simplex virus types 1 and 2 diseases.

DESCRIPTION OF THE INVENTION

The antiviral activity of racemic 2, with clofibric acid serving as positive control, is compared to the aci-reductones 4-spiro-2-hydroxytetronic acid 4 and benzopyranones 5-8 not possessing antilipidemic activity (Witiak et al., *J. Med. Chem.*, 31:1437 (1988)). Antiviral properties were examined against the enveloped virus HSV-2. One analogue of this series, namely, 3,4-dihydroxy-2H-benzopyrane-2-one (5), exhibited anti-HSV-2 properties at noncytotoxic concentrations and was studied in greater depth against HSV-1, vesticular stomatitis virus (VSV), and poliovirus-2. HSV-1 and 2 and VSV, but not poliovirus-2, are enveloped viruses.

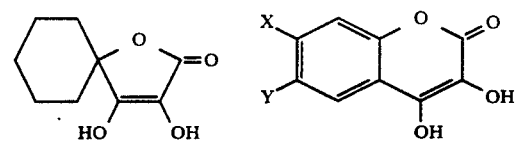

4

5, X = Y = H
6, X = H, Y = Cl
7, X = H, Y = OH
8, X, Y = OCH$_2$O

An operational distinction exists between compounds that act extracellularly verus those that act intracellularly. This distinction must be taken into consideration in the design and development of antiviral agents. Compounds that act intracellularly are often targeted to interfere with viral nucleic acid metabolism. Often such antiviral agents are structural analogues for nucleic acid synthesis, and can lead to the development of resistant viral mutants, exhibit mutagenic or teratogenic activities, and/or suppress the immune system.

Little consideration has been given to compounds that act extracellulary because many viruses are resistant to compounds that would be toxic to host cells. However, alternative safe approaches are needed for the inactivation of viruses found in clinical specimens, on body surfaces or in body fluids such as seminal and genital secretions. Several apparently non-toxic compounds have extracellular activity against enveloped viruses. For example, at concentrations of 0.07–0.16 mM butylated hydroxytoluene (BHT), a compound used as a food additive, causes 50% inactivation of HSV as discussed in Snipes et al., Science, 188:64 (1975). BHT is a highly fat soluble antioxidant that may perturbate membrane associated functions. Viruses that contain lipids are readily inactivated by BHT, whereas viruses having no lipids are comparatively insensitive.

Lipophilic alcohols (decanol, dodecanol, tetradecanol) also produce 90–100% extracellular inactivation of HSV at concentrations of 0.5 mM, and phytol inhibits HSV at 0.01–0.1 mM as well as enveloped virus $\phi$ 6 at $10^{-6}$ to $10^{-4}$ mM concentrations. One lipid compound, AL721 discussed in Sarin et al., N. Eng. J. Medicine 313:1289 (1985), composed of glycerides, phosphatidylcholine and phosphatidylethanolamine in a 7:2:1 ratio, when used at 20 μg/ml concentrations is virucidal for the human immunodeficiency virus (HIV). Activity at this concentration is comparable to AL721's potency in extracting cholesterol from peripheral blood lymphocytes as discussed in Lyte et al., Biochim. Biophys. Acta, 812:133 (1985), but it is not known whether this lipid has an action on the retroviral envelope or on the host cell membrane. The spermicidal surfactants nonoxynol-9 discussed in Polsky et al., Lancet, i, 1456 (1988) and benzalkonium chloride (BC) discussed in Wainberg et al., J. Clin. Microbiol., 28:156 (1990), also inactivate HIV. Nonoxynol-9 is a non-ionic surfactant used at 1-5% (w/w) concentrations in spermicides, whereas the cationic surfactant BC destroys the infectiousness of HIV in general fluids of seropositive individuals at concentrations of 0.05%.

Kessler et al., Antimicrob. Agents Chemother., 20:826 (1981), found that treatment of the lipid-enveloped hepatitis B virus (HBV) with increasing does (5-250 μg/mL) of the mammalian cell membrane cholesterol-binding (Medoff et al., The Polyenes, In Antifungal Chemotherapy, Speller, D., ed., John Wiley and Sons Ltd., London, (1980) p. 3-33) polyene antibiotic amphotericin B leads to a concentration dependent increase in HBV DNA polymerase activity, changes in electron microscopic appearance of the virus, increased penetration of negative stain into the lipid envelope, disruption of the particle and an increase in density from 1.165–1.225 g/mL. Viral disruption results in the formation of a nonparticulate HBV surface-antigen-reactive fraction and an amphotericin beta-antigen complex fraction with no respective antigen immunoreactivity. Ketoconazole, an imidazole antifungal agent that interfers with sterol and lipid biosynthesis, non-specifically inhibits HBV surface antigen production as discussed in Pottage, Jr., et al., J. Med. Virol. 16:275 (1985), which was paralleled by a decrease in cellular protein synthesis. Ketoconazole is most active and specific causing a 72% inhibition in antigen production with only a 38% reduction in protein synthesis at 10 μg/mL concentrations. The polyene antibiotic filipin also inactivates enveloped viruses presumably owning to its interaction with sterols thereby causing alterations in the lipid bilayer structure.

The present invention discloses that the aci-reductone 3,4-dihydroxy-2H-1-benzopyran-2-one compound is active against HSV. Solutions of this compound stored at 4° C. for 2 months possess similar antiviral activity as freshly prepared material. At a non-toxic concentration (10 μM), this aci-reductone exhibits both intracellular and extracellular activity against HSV-1 and HSV-2. Even though extracellular activity (81%) is significantly higher than intracellular (36%) inhibition of plaque formation, no reduction in plaque size is seen when the virus is treated extracellularly. The fact that inhibition in plaque formation is found both intracellularly and extracellularly, but reduction in plaque size is observed only intracellularly indicates a dual mechanism of action. The aci-reductone has an effect on the early states of HSV replication such as adsorption or penetration as well as on a later virus induced event, thus making this compound useful for both internal and topical administration.

The aci-reductone 3,4-dihydroxy-2H-1-benzopyran-2-one (compound 5) was selective for HSV among the viruses tested. The aci-reductone compound 5 was investigated to determine its mode of action against HSV, and the spectrum of antiviral activity. Mechanistic possibilities include inactivation of envelope proteins, membrane lipid perturbation, and interuption of lipid-protein interactions. Compounds active against both human immunodeficiency virus (HIV) and HSV could be used to treat blood samples or other specimens to render them non-infectious, thereby reducing the risk of laboratory workers to contaminated materials. Furthermore, the aci-reductone compounds may complement the activity of other agents in spermicidal jellies, suppositories and lubricants for condoms.

The following examples illustrate the present invention. These examples are not intended to limit the scope of the present invention in any manner.

EXAMPLE 1

The cytotoxic effect of the compounds tested is determined by monitoring the uptake of [$^3$H]-thymidine, a precursor for DNA synthesis. Buffalo green monkey kidney (BGM 70) cells are seeded in 96-well microliter plates and allowed to grow in a growth medium consisting of 10% fetal bovine serum (FBS), 10% Eagles Minimal Essential Medium (EMEM) and 1.2% NaHCO$_3$ until they reach 80–90% confluency. Analogues are dissolved in 1% NaOH solution and the pH is adjusted to 7.0 with 1N HCl. Various drug concentrations are prepared in maintenance medium consisting of 2% FBS, 10% EMEM, and 2% NaHCP$_3$. Following addition of 200 μL drug preparations, cells are incubated at 37° C. for 27, 48 and 72h, and pulsed with 1 μCi of [$^3$H]-thymidine for the last 24h of any given incubation period. After incubation, cells are trypsinized and collected with a MASH-II cell harvester. Exogenous isotope is removed by exhaustive washing with saline. A Beckman LS-7000 liquid scintillation counter is used to determine radioactivity. The percentage of inhibition of [$^3$H]-labeled precursor uptake is determined as follows; percent inhibition=100 (mean CPM of drug treated cultures divided by mean CPM of non-drug-treated cultures).

The inhibition of [$^3$H]-thymidine uptake and inhibition of cell growth are used as indicators of toxicity. Table 1 below shows the effect of 6 compounds at different concentrations (0.4 to 100 μM) on [$^3$H]-thymidine uptake and/or cell growth. 3,4-Dihydroxy-2H- benzopyran-2-ones 5 and 8 exhibit no toxicity at a concentration of 10 μM, whereas, related compounds 1 (R=Me, Ar=p—ClPh), 4, 6 and 7 display toxicity at concentrations of 10 μM or less.

(P<0.01) when HSV-2 is treated at 10 μM concentrations prior to cell infection. When washed virus-infected cells are treated with 10 μM concentrations of this drug, as seen in Table 1, for 48 hours as a measure

TABLE 1

Effect of Potential Antiviral Compounds on Herpes Simplex Virus (HSV)-2 Replication

| Cmpd | Conc. (μmol/L) | % Inhibition of [$^3$H]-Thymidine$^a$ Incorporated 24 h | 48 h | 72 h | % Reduction$^b$ of cell growth 24 h | 48 h | % Inhibition of PFU$^c$ IA$^d$ | EA$^e$ |
|---|---|---|---|---|---|---|---|---|
| 1$^f$ | 10.0 | 95.0 ± 0.4$^g$ | 98.6 ± 0.5 | 98.2 ± 0.8 | ND$^h$ | ND | ND | ND |
|  | 2.5 | 66.7 ± 5.8 | 74.3 ± 9.3 | 53.9 ± 16.3 | 60.0 ± 9.1 | 90.0 ± 4.6 | ND | ND |
|  | 1.6 | 16.7 ± 12.7 | 14.5 ± 15.5 | 39.9 ± 15.7 | 54.0 ± 8.6 | 67.0 ± 12.1 | 8.0 ± 2.4 | 1.5 ± 0.1 |
|  | 0.4 | 0 | 0 | 0 | 12.0 ± 4.0 | 16.0 ± 3.6 | 0 | 0 |
| 4 | 10.0 | ND | ND | ND | 88.0 ± 6.1 | 86.0 ± 6.1 | ND | ND |
|  | 2.5 | ND | ND | ND | 37.0 ± 9.4 | 59.0 ± 12.4 | ND | ND |
|  | 1.6 | ND | ND | ND | 21.0 ± 12.0 | 22.0 ± 6.1 | ND | 1.8 ± 0.2 |
|  | 0.4 | ND | ND | ND | 6.0 ± 1.1 | 8.4 ± 3.6 | ND | 2.0 ± 1.0 |
| 5 | 100.0 | ND | ND | ND | 47.8 ± 9.0 | 54.1 ± 3.2 | ND | ND |
|  | 50.0 | ND | ND | ND | 5.9 ± 0.5 | 8.7 ± 2.8 | ND | ND |
|  | 10.0 | 28.4 ± 7.6 | 26.3 ± 6.3 | 0 | 0 | 0.4 ± 0.0 | 36.0 ± 4.7 | 81.0 ± 4.0 |
|  | 2.5 | 0 | 0 | 0 | ND | ND | ND | ND |
|  | 1.6 | 0 | 0 | 0 | ND | ND | ND | ND |
|  | 0.4 | 0 | 0 | 0 | ND | ND | ND | ND |
| 6 | 10.0 | 90.0 ± 1.4 | 99.2 ± 0.8 | 99.2 ± 0.8 | ND | ND | ND | ND |
|  | 2.5 | 17.8 ± 2.0 | 20.0 ± 3.3 | 17.0 ± 5.0 | 56.0 ± 12.0 | 58.0 ± 9.4 | ND | 0.4 ± 0.1 |
|  | 1.6 | 31.1 ± 5.8 | 46.8 ± 9.0 | 41.4 ± 14.0 | 20.0 ± 6.2 | 30.0 ± 13.1 | 10.0 ± 4.6 | 1.2 ± 0.6 |
|  | 0.4 | 11.1 ± 9.1 | 16.7 ± 8.4 | 31.8 ± 12.0 | 21.0 ± 1.0 | 12.0 ± 6.5 | 3.0 ± 1.1 | 1.5 ± 0.8 |
| 7 | 100.0 | ND | ND | ND | 52.0 ± 8.0 | 66.0 ± 11.1 | ND | ND |
|  | 50.0 | ND | ND | ND | 18.4 ± 6.1 | 22.1 ± 8.4 | ND | ND |
|  | 10.0 | 44.3 ± 9.1 | 46.6 ± 8.0 | 48.4 ± 14.0 | 1.6 ± 0.2 | 2.0 ± 1.0 | 10.0 ± 3.2 | 86.0 ± 0.5 |
|  | 2.5 | 36.9 ± 8.6 | 37.2 ± 5.1 | 39.3 ± 13.1 | 0.4 ± 0.0 | 1.0 ± 0.4 | ND | ND |
|  | 1.6 | 28.6 ± 12.0 | 31.7 ± 8.4 | 31.6 ± 8.4 | ND | ND | ND | ND |
|  | 0.4 | 13.6 ± 6.1 | 13.9 ± 6.1 | 13.9 ± 6.1 | 14.2 ± 6.2 | ND | ND | ND |
| 8 | 100.0 | ND | ND | ND | 68.0 ± 7.6 | 71.0 ± 8.1 | ND | ND |
|  | 50.0 | ND | ND | ND | 54.0 ± 2.0 | 52.2 ± 9.1 | ND | ND |
|  | 10.0 | ND | ND | ND | 6.6 ± 1.0 | 8.1 ± 2.1 | 6.1 ± 1.0 | 16.0 ± 8.0 |
|  | 2.5 | ND | ND | ND | 2.0 ± 0.6 | 4.2 ± 3.6 | 1.0 ± 0.2 | 3.0 ± 1.0 |

Footnotes to Table 1
$^a$After each incubation period, cells are trypsonized, collected with a MASH-II cell harvester and placed in a scintillation counter to determine incorporation of labelled compound and level of toxicity. BGM 70 cells are seeded at a concentration of 270 cells per well in a 24-well tissue culture plate. Cells are planted in 2 mL of growth medium with or without the test compound and are incubated at 37° C. for 38 hours. At 24 hours medium is removed from one-half of the plates and the cells are fixed and stained with crystal violet. The remaining cultures are fixed and stained at 48 hours.
$^b$BGM 70 cells are counted microscopically and comparisons are made. Experiments are performed blindly by assigning each compound concentration a letter code. The code is broken after the cells are counted.
$^c$Plaque forming units.
$^d$Intracellular activity. BGM 70 cells are grown until they reach 80% confluency. Monolayers are then infected, washed 3 times with EBSS. Maintenance medium with or without compound is added. Monolayers are stained after 48 hours and the number PFU$^c$ is determined. The experiment is performed blindly by assigning a letter code. The code is broken after the plaques are counted.
$^e$Extracellular activity. Virus is incubated in the presence of the compound. BGM 70 cells are then infected and the monolayers are washed 3 times with EBSS. Cells are stained after 48 hours. The experiment is performed blindly.
$^f$R=Me, Ar=p-ClPh is structure 1.
$^g$Standard deviation.
$^h$Not determined.

EXAMPLE 2

The effect of the compounds on the inhibition of cell growth is determined using BGM-70 cells grown in vitro. For this assay, BGM 70 cells are seeded at a concentration of approximately 70 cells per well in 24-well tissue culture plates. Cells are planted in 2 ml of growth medium with or without the test compound and are incubated at 37° C. for 48 hours. At 24 hours, cells from one half of the plates are fixed and stained with crystal violet. The remaining cultures are fixed and stained at 48 hours. Cells are counted microscopically and comparisons are made between non-treated (control) and treated cells.

At non-toxic concentrations all compounds tested except for aci-reductone 5 show little or no activity against HSV-2. A series of experiments, as shown in Table IV, were performed to determine the intracellular and extracellular effect of aci-reductone 5 against HSV. When HSV-2 is incubated in the presence of this compound (i.e., extracellularly), a marked reduction in plaque forming units (PFU) occurs. Results from 6 independent experiments show an 81% reduction of intracellular activity only a 36% reduction (P<0.01) in PFU occurs. Clofibric acid (2, R=R$_1$=Me, Ar=p—ClPh), previously was observed to have anti-HSV-1 activity (45% inhibition) at 500 μM concentrations, Mehl, supra., and in this experiment serves as a positive control for comparison with benzopyranone 5. Thus, in one experiment (n=3 wells), clofibric acid exhibits 66+/−6% (P<0.02) inhibition at 500 μM with aci-reductoine 5 exhibiting 26+/−4% (P<0.07) inhibition at 10 μM concentrations using virus-infected cells. With extracellular treatment of HSV-2, clofibric acid (500 μM) produces no significant (P>0.05) inhibition, but compound 5 exhibits 63+/−4% (P<0.01) inhibition.

EXAMPLE 3

The inactivation of herpes simplex virus (HVS)-1 and 2 by 3,4-dihydroxy-2H-1-benzopyran-2-one (compound 5) was tested.

Table II summarizes the experiments wherein the effect of aci-reductone 5 is comparatively evaluated against both HSV-1 and HSV-2. Extracellularly, a significant reduction (76-98%; P<0.01) is observed at the 10 μM level against both HSV-1 and HSV-2. Intracellularly, compound 5 is less effective ranging from 25-39% (P<0.01) inhibition at 10 μM concentrations. These results are not affected by 10-fold differences in viral concentrations.

TABLE II

Inactivation of Herpes Simplex Virus (HSV)-1 and 2 by 3,4-Dihydroxy-2H-1-benzopyran-2-one (5)

| Treatment[a] | Relative Viral Conc | Plaque Forming Units Mean ± SD | % Inhibition |
|---|---|---|---|
| HSV-1 control[b] | 100 | 172.0 ± 8.2 | — |
|  | 10 | 14.6 ± 0.5 | — |
| HSV-1 + Vehicle[c] | 100 | 169.0 ± 10.2 | 2 |
|  | 10 | 16.0 ± 3.6 | 10 |
| HSV-2 Control[d] | 100 | 214.6 ± 9.3 | — |
|  | 10 | 21.3 ± 2.3 | — |
| HSV-2 + Vehicle[e] | 100 | 207.0 ± 3.6 | 3 |
|  | 10 | 19.7 ± 1.5 | 8 |
| HSV-1 + 1 × Cmpd[f] | 100 | 40.6 ± 3.8[g] | 76 |
|  | 10 | 2.6 ± 1.6[g] | 82 |
| HSV-2 + 1 × Cmpd[h] | 100 | 49.3 ± 4.5[i] | 77 |
|  | 10 | 5.3 ± 1.5[i] | 64 |
| HSV-1 + 2 × Cmpd[j] | 100 | 9.3 ± 1.5[g] | 95 |
|  | 10 | 0.3 ± 0.5[g] | 98 |
| HSV-2 + 2 × Cmpd[k] | 100 | 9.7 ± 1.5[i] | 95 |
|  | 10 | 0.6 ± 0.6[i] | 96 |
| HSV-1: 1 × Cmpd[l] | 100 | 106.6 ± 9.3[g] | 38 |
|  | 10 | 11.0 ± 1.0 | 25 |
| HSV-2: 1 × Cmpd[m] | 100 | 153.6 ± 7.4[i] | 39 |
|  | 10 | 14.3 ± 1.1 | 33 |

Table II-Footnotes
[a]The experiment is performed blindly. Each compound concentration is assigned a letter and the code is broken after the plaques are counted.
[b]HSV-1 is incubated in the presence of EBSS for 2 hours. Buffalo green money kidney (BGM-70) cells are then infected and the monolayers are washed with EBSS after the 2 hour adsorption period. Cells are stained after 48 hours with crystal violet.
[c]Same as (b), but the virus is incubated in the presence of pH adjusted vehicle.
[d]Same as (b), but HSV-2 is used instead of HSV-1.
[e]Same as (d), but virus is incubated in the prescene of pH adjusted vehicle.
[f]HSV-1 is incubated in the presence of freshly made 1 × compound (10 μM). Mixtures are then diluted and BGM 70 cells are infected. Monolayers are washed after the adsorption period and stained with crystal violet after 48 hours of incubation.
[g]A statistical difference with N = 3 (No. of wells) between (b) and (f); (b) and (j); (b) and (l) using Student's test with a P < 0.01.
[h]Same as (f), but HSV-2 is used instead of HSV-1.
[i]A statistical difference with N = 3 (No. of wells) is seen between (d) and (h); (d) and (k); (d) and (m) using Student's test with a P-value < 0.01.
[j]Same as (f), but with 2 × Compound (20 μM).
[k]Same as (h), but with 2 × Compound.
[l]BGM 70 cells are grown until they reach 80% confluency. Monolayers are infected with HSV-1, washed with EBSS, and then maintenance medium with 1 × Compound is added. Monolayers are stained after 48 hours.
[m]Same as (l) but HSV-2 is used.

EXAMPLE 4

For antiviral studies the diameter of plaques is determined with the aid of a calibrated micrometer slide and a microscope eye piece having scaled markings. A simple random sample is taken and all plaque diameters are measured for both experimental and control groups.

Plaque diameter also serves as an indication of inhibition of viral replication. A significant reduction in plaque size (56%) is seen when compound 5 (10 μM) is used in viral-infected cell experiments, whereas no significant reduction is observed when virus is treated extracellularly with this concentration of drug, as shown in Table III below. At 20 μM concentrations similar results are observed. These results are also not affected by 10-fold differences in viral concentrations.

TABLE III

Effect of 3,4-Dihydroxy-2H-1-benzopyran-2-one (5) on Herpes Simplex Virus (HSV)-2 Plaque Size

| Comp Conc (μM) | Relative Viral Conc | Mean plaque diameter (±SD)[a] Intracellularly[b] | | | Mean plaque diameter (±SD) Extracellularly[c] | | |
|---|---|---|---|---|---|---|---|
| | | Control | Treated | % Inhib | Control | Treated | % Inhib |
| 10 | 10 | 502 ± 126 | 221 ± 89[d] | 56 | 502 ± 126 | 500 ± 100 | 1 |
| 10 | 1 | 479 ± 98 | 213 ± 79[d] | 56 | 479 ± 98 | 449 ± 70 | 6 |
| 20 | 10 | 497 ± 89 | 202 ± 88[d] | 60 | 497 ± 89 | 486 ± 80 | 1 |
| 20 | 1 | 506 ± 103 | 205 ± 90[d] | 60 | 506 ± 103 | ND[e] | ND |

Table III - footnotes
[a]Plaque diameters are expressed in micrometers +/− standard deviation.
[b]Buffalo Green Monkey Kidney (BGM-70) cells are grown until they reach 80% confluency. Monolayers are then infected, washed with EBSS and maintenance medium with or without compound added. Cells are stained after 48 hours with crystal violet and the plaque diameters are determined with the aid of a micrometer.
[c]Virus is incubated with or without the compound. Mixtures are then diluted, and BGM 70 cells are infected. Monolayers are washed with EBSS, stained with crystal violet after 48 hours and plaque diameters determined.
[d]A statistical difference with N = 36 (No. of plaques) is seen between control and treated samples using Student's t test with P < 0.001 for both concentrations tested.
[e]Not determined.

EXAMPLE 5

The antiviral activity of each compound was tested against HSV-2, and the most active benzopyranone 4 at non-toxic concentrations was also tested against poliovirus-2, HSV-1, and VSV using a similar protocol. The protocol employs twelve well plates which are seeded with BGM 70 cells and allowed to grow until they reach approximately 80% confluency. Growth medium is then removed, and the virus is allowed to adsorb for 2 hours at 37° C. After adsorption, maintenance medium with or without the drug is added and the plates are reincubated for 48 hours. Cell monolayers are then stained with 0.5% crystal violet in 10% formaldehyde, and PFU are determined for control and experimental groups.

The extracellular effect of a compound on the virus is determined by incubating the virus with or without the compund for 2 hours at 37° C. Virus-compound mixtures are diluted (>10,000-fold) in order to reduce drug concentrations to levels shown to have no intracellular antiviral activity. The 80% confluent monolayers are then infected with the diluted virus mixtures. Following infection, the monolayers are washed 3× with Earles Balance Salt Solution (EBSS). After 48 hours, monolayers are fixed and stained with crystal violet as described herein.

The results are clearly shown in Table IV below. The compound 5 shows both intra- and extra- cellular antiviral activity against HSV-1 and HSV-2. However, compound 5 exhibits no antiviral activity either intra- or extra-cellularly when assessed against either poliovirus-2 or VSV(n=2).

TABLE IV

Effect Virus of 3,4-Dihydroxy-2H-benzopyran-2-one (5) on HSV-1[a], HSV-2, Poliovirus-2 and VSV[b]

| Virus | % Inhibition of Plaque Forming Units | |
|---|---|---|
| | Intracellularly[c] | Extracellularly[d] |
| HSV-1 | 38.4 ± 5.7[e] | 76.4 ± 2.2[e] |
| HSV-2 | 36.0 ± 4.7[e] | 81.0 ± 4.0[e] |
| POLIOVIRUS-2 | 2.1 ± 0.0 | 2.7 ± 0.0 |
| VSV | 0 | 0 |

Table IV - footnotes
[a] Herpes simplex virus type 1.
[b] Vesicular stomatitis virus.
[c] Buffalo Green Monkey Kidney (BGM-70) cells are grown until they reach 80% confluency. Monolayers are then infected and washed with EBSS. Maintenance medium containing 10 µM compound is added. Monolayers are stained after 48 hours.
[d] Virus is incubated in the presence of 10 µM compound. The mixtures are then diluted, and BGM-70 cells are infected. Monolayers are washed with EBSS after 1 hour adsorption and stained after 48 hours.
[e] A significant difference is seen between treated and non-treated cells for HSV-1 and HSV-2, $P < 0.01$.

The 3,4-dihydroxybenzopyranone compound is thus useful in the treatment or prevention of infections caused by the herpes simplex viruses types 1 or 2. The invention accordingly further provide a 3,4-dihydroxybenzopyranone compound and physiologically acceptable salts for use in the therapy or prophylaxis of such viral diseases.

According to the present invention the 3,4-dihydroxybenzopyranone compound may be formulated in a conventional manner, optionally together with one or more other active ingredients, for administration by any convenient route for example for oral, topical, intraveneous or intramuscular administration.

Thus, the invention provides a pharmaceutical composition comprising the 3,4-dihydroxybenzopyranone compound and/or a physiologically acceptable salt thereof together as the active ingredient with a physiologically acceptable carrier or excipient. It is within the contemplated scope of the invention that the active ingredient is present in an amount of at least about 1 to 10 percent, by weight, effective to exhbit antiviral activity.

The 3,4-dihydroxybenzopyranone compound can be administered both to humans and animals. It is contemplated that such compound can be used in veterinary applications as a feed additive, a spray or additive to an animals water supply. In addition, the 3, 4-dihydroxybenzopyranone compound can be administered to humans and animals by a variety of routes including, oral, topical, intravenous or intramuscular administrations.

For oral administration, the pharmaceutical composition may take the form of, for example, tablets, capsules, powders, solutions, syrups or suspensions prepared by conventional means with physiologically acceptable excipients.

For topical administration, the pharmaceutical composition may take the form of, for example, creams, lotions, gels, ointments, salves or foams prepared by conventional means with physiologically acceptable excipients.

The compounds may be formulated for intravenous or intramuscular administration in dry form for reconstitution before use, or as a sterile solution or suspension.

Physiologically acceptable salts of the 3,4-dihydroxybenzopyranone compound may be prepared by reacting the acid of the benzopyranone with an appropriate base such as for example, NaOH, KOH, $Na_2CO_3$, or $(NH_4)_2CO_3$, in the presence of a suitable solvent to obtain the desired physiologically acceptable salt.

The benzopyanone compound may be prepared by a number of processes, including those processes disclosed in the Witiak et al., U.S. Pat. No. 4,845,121 issued Jul. 4, 1989 which is expressly incorporated herein by reference.

The above description and examples fully disclose this invention and the preferred embodiments thereof. The invention, however, is not limited to the precise constructions herein described but, rather, encompasses all modifications and improvements coming within the scope of the claims which follow.

We claim:

1. A method for treating infectious viral diseases caused by herpes simplex virus types 1 or 2 comprising administering to a host having the viral diseases a pharmaceutical composition containing as an active ingredient 3,4-dihydroxy-2H-benzopyran-2-one in association with a pharmaceutically acceptable carrier, the active ingredient being present in a therapeutically effective amount to exhibit antiviral activity.

2. A method for inhibiting viral infections causes by herpes simplex virus types 1 or 2 comprising administering to a host having the viral disease a pharmaceutical composition containing as an active ingredient 3,4-dihydroxy-2H-benzopyran-2-one in association with a pharmaceutically acceptable carrier, the active ingredient being present in a therapeutically effective amount to exhibit antiviral activity.

3. The method of claim 1, comprising administering to the host the pharmaceutical composition in an orally administrable form.

4. The method of claim 1, comprising administering to the host the pharmaceutical composition in an internally administrable form.

5. The method of claim 1, comprising administering to the host the pharmaceutical composition in a topically administrable form.

6. The method of claim 5 comprising administering the pharmaceutical composition in combination with at least one spermicidal jelly.

7. The method of claim 5 comprising administering the pharmaceutical composition in combination with at least one suppository.

8. The method of claim 5 comprising administering the pharmaceutical composition in combination with at least one lubricant for a condom.

* * * * *

UNITED STATES PATENT AND TRADEMARK OFFICE
CERTIFICATE OF CORRECTION

PATENT NO. : 5,185,366
DATED : Feb. 9, 1993
INVENTOR(S) : Donald T. Witiak, John H. Hughes and Charis T. Mavromoustakis It is certified that error appears in the above—identified patent and that said Letters Patent is hereby corrected as shown below:

Item [54],
Title page, title of invention, last line, "2H" should be --2--;

Column 1, title of invention, line 6, "2H", second occurrence, should be --2--;

Column 2, line 24, "2" should be --2H--;

Column 2, line 25, "2H" should be --2--.

Signed and Sealed this

Twenty-second Day of November, 1994

Attest:

BRUCE LEHMAN

Attesting Officer     Commissioner of Patents and Trademarks